(12) United States Patent
Campin et al.

(10) Patent No.: US 6,394,605 B1
(45) Date of Patent: May 28, 2002

(54) FOGGING METHOD FOR A WAVEFRONT SENSOR

(75) Inventors: John A. Campin; Gary P. Gray, both of Orlando; George H. Pettit, Maitland, all of FL (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/863,561

(22) Filed: May 23, 2001

(51) Int. Cl.$^7$ .................................................. A61B 3/00
(52) U.S. Cl. ........................................................ 351/246
(58) Field of Search ................................. 351/200, 205, 351/211, 212, 221, 246; 606/4, 5

(56) References Cited

U.S. PATENT DOCUMENTS 5,442,412 A    8/1995   Frey et al.
5,632,742 A    5/1997   Frey et al.
5,777,719 A    7/1998   Williams et al.
5,949,521 A    9/1999   Williams et al.
6,095,651 A    8/2000   Williams et al.
6,155,684 A  * 12/2000   Bille et al. .................. 351/212

FOREIGN PATENT DOCUMENTS

WO         WO 00/10448         3/2000

* cited by examiner

Primary Examiner—George Manuel
(74) Attorney, Agent, or Firm—Jeffrey S. Schira

(57) ABSTRACT

An automated focusing method for a wavefront sensor that iteratively determines the best optics setting for the wavefront sensor by making objective measurements of the patient's focus without the need for subjective information from the patient.

3 Claims, 2 Drawing Sheets

FOGGING METHOD FOR A WAVEFRONT SENSOR

BACKGROUND OF THE INVENTION

This invention relates generally to the field of laser refractive surgery and, more particularly, to wavefront sensors used as diagnostic devices in laser refractive surgery.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has gained widespread acceptance is radial and/or transverse incisional keratotomy (RK or AK, respectively). In the 1990s, the use of photoablative lasers to reshape the surface of the cornea (photorefractive keratectomy or PRK) or for mid-stromal photoablation (Laser-Assisted In Situ Keratomileusis or LASIK) have been approved by regulatory authorities in the U.S. and other countries.

In the past, the amount of tissue removed by the laser was determined by taking pre-operative measurements of the optical errors of the eye, sphere, cylinder and axis, termed "low order" optical aberrations. These measurements were manually loaded into the refractive laser and a proposed corrective "recipe" was calculated by the laser software. More recently, the use of wavefront sensor technology, which measures both the low order optical aberrations and the "higher" order aberrations, such as coma, trefoil and spherical aberration, have been investigated. See for example U.S. Pat. Nos. 5,777,719, 5,949,521, 6,095,651 (Williams, et al.), U.S. patent application Ser. Nos. 09/566,409 and 09/566,668, both filed May 8, 2000, and in PCT Patent Publication No. WO 00/10448, the entire contents of which being incorporated herein by reference. These wavefront sensors are particularly useful when used in combination with a high-speed eye movement tracker, such as the tracker disclosed in U.S. Pat. Nos. 5,442,412 and 5,632,742 (Frey, et al.), the entire contents of which being incorporated herein by reference. The ultimate goal of these devices is to link the wavefront sensor to the laser and eye movement tracker to provide real-time diagnostic data to the laser during surgery. In the past, as best seen in FIG. 1, in order to focus wavefront sensing device 10, the patient was seated at the device so that the patient's eye 12 views fixation target 14 though optical pathway 16 that includes adjustable focus mechanism 18. Mechanism 18 compensates for defocus error (and possibly astigmatism) to allow the patient to see fixation target 14 relatively clearly regardless of the refractive error in the patient's eye 12. Video camera 20, disposed along optical pathway 22 allows device 10 operator (not shown) to position eye 12 relative to device 10. Once the patient is in the correct position and is viewing fixation target 14, probe beam 24 of optical radiation is sent into eye 12. A fraction of the radiation is scattered by the retina exits the eye in the form of a re-emitted wavefront. Optical pathway 26 conveys this wavefront to the entrance face of wavefront sensor 28.

The lens of the eye is a dynamic element, capable of changing the effective focal length of the eye through accommodation. In performing wavefront measurements, it is important to take this accommodative ability into account. Normally, the wavefront is measured with the lens as relaxed as possible, so that the eye is minimally refracting (most hyperopic). Relaxing the lens is typically achieved by adjusting the focus mechanism in the fixation pathway so that the fixation target appears to lie just beyond the patient's most hyperopic focal point. The fixation target in this instance will appear slightly out of focus to the patient. This process is known as "fogging".

Prior to the present invention, fogging for a wavefront sensor was typically performed manually in one of two ways. One method involves subjective feedback from the patient, wherein the optics are adjusted until the patient reports that the fixation target appears to be in best focus. The optics are then adjusted in the hyperopic direction by a larger amount, so that the fixation target appears to lie well beyond the patient's most relaxed focal plane and the patient reports that the fixation target is no longer discernable. Finally, the optics are adjusted in the myopic direction until the patient reports that the fixation target is just discernable, but still substantially blurred.

Alternatively, the device operator can attempt to fog the patient's eye by viewing a pattern of focused light spots from the wavefront camera and adjusting the fixation target until the spots seem as widely separated as possible, indicating that the eye is maximally relaxed.

Both of these prior art methods require subjective determination, by either the patient of the operator, as to the best optics setting, and require substantial participation by a skilled operator.

Accordingly, a need continues to exist for a focusing method for a wavefront sensor that does not require subjective assessment of the best optics setting and does not require manipulation for a skilled operator.

BRIEF SUMMARY OF THE INVENTION

The present invention improves upon the prior art by providing an automated focusing method for a wavefront sensor that iteratively determines the best optics setting for the wavefront sensor by making objective measurements of the patient's focus without the need for subjective information from the patient.

Accordingly, one objective of the present invention is to provide an automated focusing method for a wavefront sensor.

Another objective of the present invention is to provide a focusing method for a wavefront sensor that does not require subjective determination of the best optic setting.

Another objective of the present invention is to provide a focusing method for a wavefront sensor that does not require participation by a skilled operator.

These and other advantages and objectives of the present invention will become apparent from the detailed description and claims that follow.

DETAILED DESCRIPTION OF THE INVENTION

Figure 1:
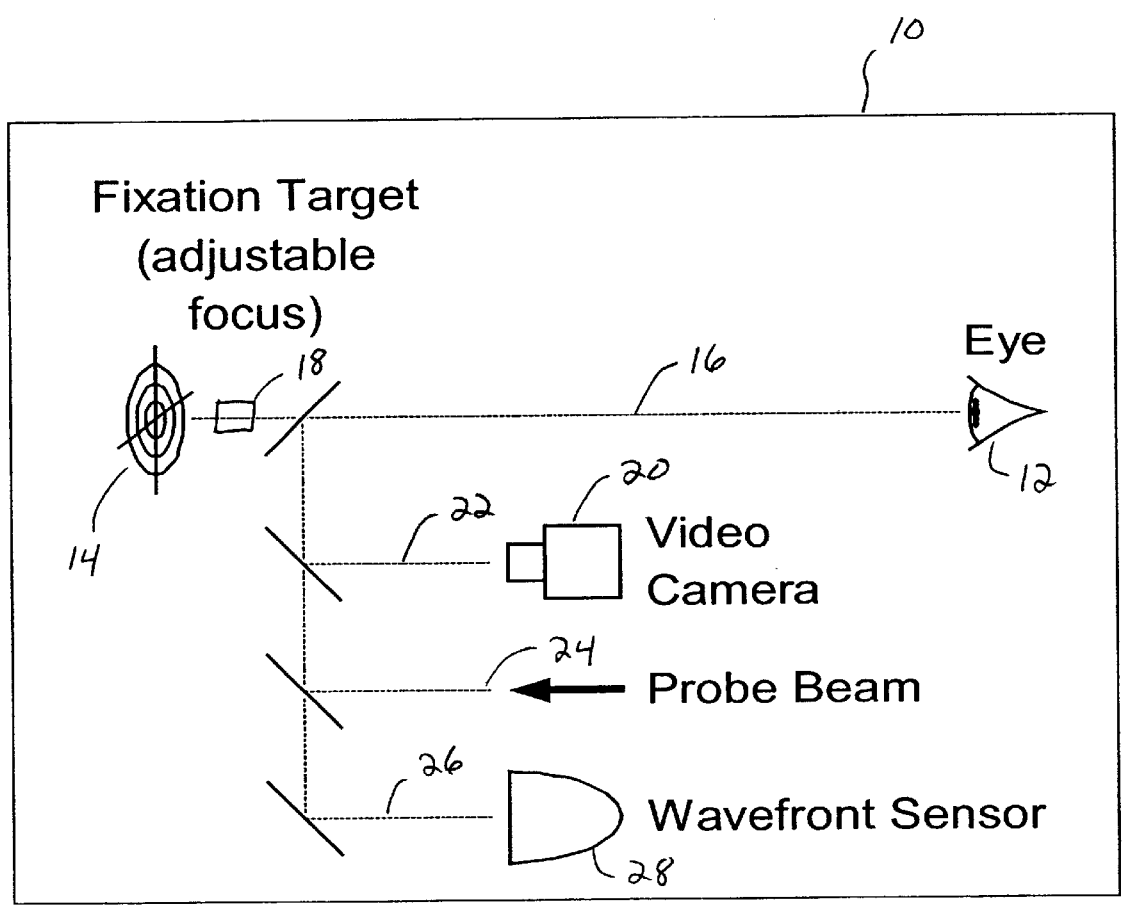
FIG. 1 is a simplified schematic representation of a prior art wavefront sensing device.
Figure 2:
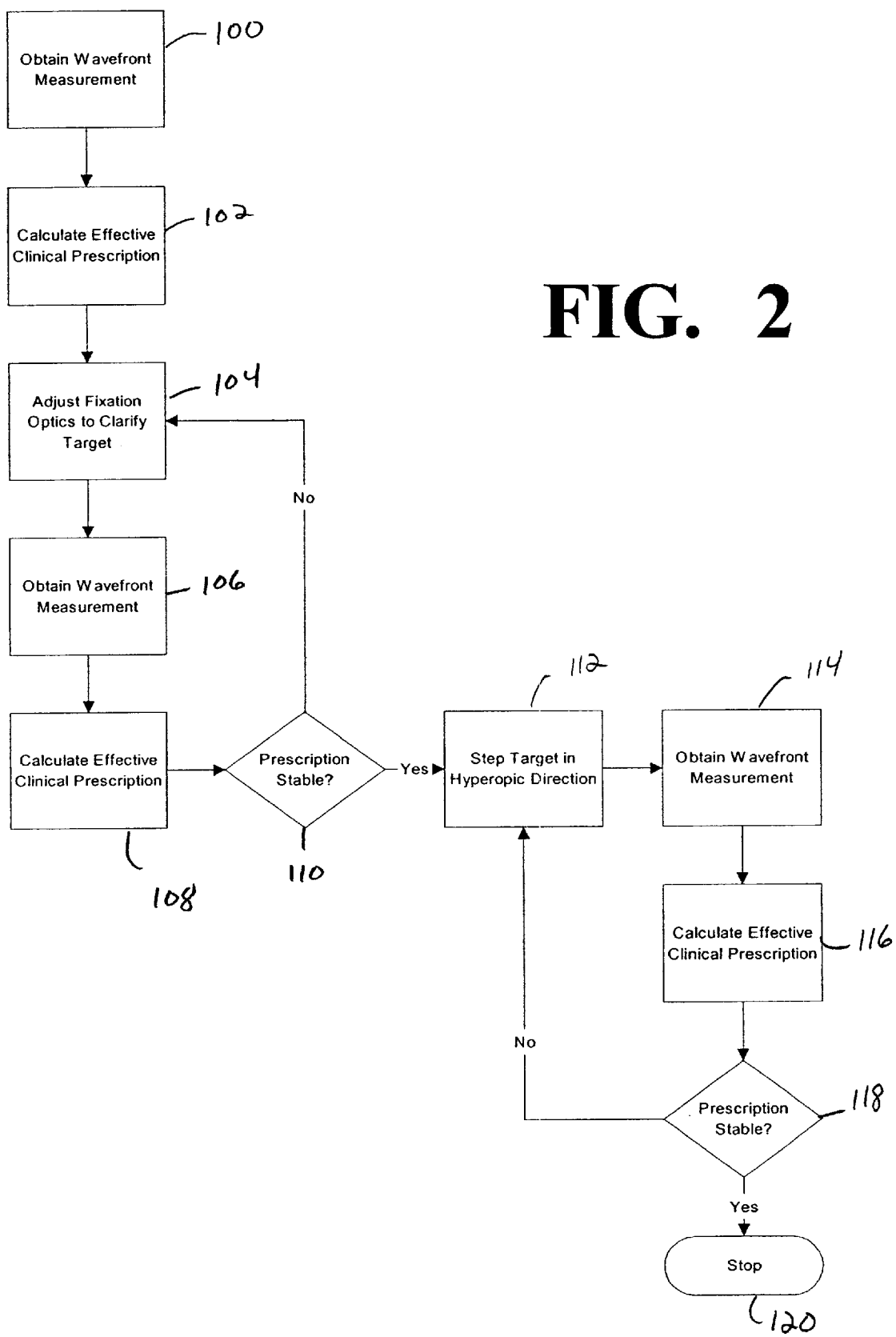
FIG. 2 is a flow chart illustrating the method of the present invention.

The focusing method of the present invention may be practiced on any commercially available wavefront sensor having appropriate software controls. Suitable devices are disclosed in U.S. Pat. Nos. 5,777,719, 5,949,521, 6,095,651, U.S. patent application Ser. Nos. 09/566,409 and 09/566,668, both filed May 8, 2000, and in PCT Publication No. WO 00/10448. As best seen in FIG. 2, the focusing method of the present invention involves an iterative process wherein the wavefront sensor first calculates a stable effective clinical prescription for the eye being measured. The prescription is then moved in the hyperopic direction until the emanating wavefront is stable at the eye's most hyperopic state.

The present invention involves initially having the patient view fixation target 14 with focus mechanism 18 in its nominal position, which is the appropriate position for an eye with no significant defocus or astigmatic error. As patient eye 12 attempts to view this target, initial wavefront measurement is taken at step 100. The effective clinical prescription for eye 12 is calculated at step 102 from the measurement taken at step 100 and focus mechanism 18 is adjusted at step 104 based on the prescription calculated at step 102. A second wavefront measurement is taken at step 106 and the effective clinical prescription for eye 12 is calculated at step 108 from the measurement taken at step 106. The difference between the prescription calculated at step 102 and the prescription calculated at step 106 is determined during step 110. If the two prescriptions are not within an allowed tolerance, such as approximately 0.25 diopters (other tolerances may also be used), steps 104 through 110 are repeated iteratively until a stable prescription is obtained (e.g., the difference between the two prescription is within the allowed tolerance).

Once a stable prescription is obtained at step 110, focusing mechanism 18 is adjusted in steps (for example, 0.5 diopters or other suitable amount) in the hyperopic direction during step 112, and an initial wavefront measurement is taken at step 114. The effective clinical prescription for eye 12 is calculated at step 116 from the measurement taken at step 114. The prescription calculated at step 116 is analyzed at step 118 to see if the prescription has also moved in the hyperopic direction by more than a threshold amount, such as approximately 0.25 diopters, or other suitable amount. If the prescription has not moved in the hyperopic direction by more than the threshold amount, then the prescription is deemed stable and eye 12 suitably fogged for accurate wavefront measurements. If the prescription has moved in the hyperopic direction by more than the threshold amount, the prescription is deemed not to be stable, and steps 112 through 118 are repeated iteratively until a stable prescription is obtained.

This description is given for purposes of illustration and explanation. It will be apparent to those skilled in the relevant art that changes and modifications may be made to the invention described above without departing from its scope or spirit. By way of example, the amount that the focusing optics of the wavefront sensor are adjusted at each iteration can vary, as can the value of the threshold amount, by any suitable value.

We claim:

1. A method of fogging an eye, comprising the steps of:
   a) taking a first wavefront measurement of an eye using a wavefront sensor;
   b) calculating a first effective clinical prescription using the first wavefront measurement;
   c) adjusting the focusing optics of the wavefront sensor in a discrete step in the hyperopic direction;
   d) taking a second wavefront measurement of the eye after adjusting the focusing optics of the wavefront sensor in the discrete step in the hyperopic direction;
   e) calculating a second effective clinical prescription using the second wavefront measurement;
   f) adjusting the focusing optics of the wavefront sensor in a further discrete step in the hyperopic direction;
   g) taking a third wavefront measurement of an eye after adjusting the focusing optics of the wavefront sensor in the further discrete step in the hyperopic direction;
   h) calculating a third effective clinical prescription using the third wavefront measurement;
   i) determining the difference between the second effective clinical prescription and the third effective clinical prescription;
   j) comparing the difference between the second effective clinical prescription and the third effective clinical prescription against an allowed tolerance; and
   k) repeating steps c) through j) until the difference between the second effective clinical prescription and the third effective clinical prescription is less than the allowed tolerance.

2. A method of fogging an eye, comprising the steps of:
   a) taking a first wavefront measurement of an eye using a wavefront sensor;
   b) calculating a first effective clinical prescription using the first wavefront measurement;
   c) adjusting the focusing optics of the wavefront sensor to compensate for the first calculated clinical prescription;
   d) repeating steps a) through c) until any change in the first effective clinical prescription is within an allowed tolerance;
   e) taking a second wavefront measurement of the eye after adjusting the focusing optics of the wavefront sensor in a first discrete step in the hyperopic direction;
   f) calculating a second effective clinical prescription using the second wavefront measurement;
   g) adjusting the focusing optics of the wavefront sensor in a further discrete step in the hyperopic direction;
   h) taking a third wavefront measurement of an eye after adjusting the focusing optics of the wavefront sensor in the further discrete step in the hyperopic direction;
   i) calculating a third effective clinical prescription using the third wavefront measurement;
   j) determining the difference between the second effective clinical prescription and the third effective clinical prescription;
   k) comparing the difference between the second effective clinical prescription and the third effective clinical prescription against an allowed tolerance; and l) repeating steps c) through j) until the difference between the second effective clinical prescription and the third effective clinical prescription is less than the allowed tolerance.

3. A method of fogging an eye, comprising the steps of:

a) obtaining a stable clinical prescription of an eye using a wavefront sensor;
b) adjusting the focusing optics of the wavefront sensor in a first discrete step in the hyperopic direction;
c) taking a first wavefront measurement of the eye after adjusting the focusing optics of the wavefront sensor in a first discrete step in the hyperopic direction;
d) calculating a first effective clinical prescription using the first wavefront measurement;
e) adjusting the focusing optics of the wavefront sensor in a further discrete step in the hyperopic direction;
f) taking a second wavefront measurement of an eye after adjusting the focusing optics of the wavefront sensor in the further discrete step in the hyperopic direction;
g) calculating a second effective clinical prescription using the second wavefront measurement;
h) determining the difference between the first effective clinical prescription and the second effective clinical prescription;
i) comparing the difference between the first effective clinical prescription and the second effective clinical prescription against an allowed tolerance; and
j) repeating steps b) through i) until the difference between the first effective clinical prescription and the second effective clinical prescription is less than the allowed tolerance.

* * * * *